United States Patent [19]

Seitzinger

[11] Patent Number: 5,357,980
[45] Date of Patent: Oct. 25, 1994

[54] SURGICAL DIAPHRAGM FOR MAINTAINING THE PNEUMOPERITONEUM DURING A LAPAROSCOPIC PROCEDURE

[76] Inventor: Michael R. Seitzinger, Rte. 7, Box 124, Santa Fe, N. Mex. 87505

[21] Appl. No.: 951,566

[22] Filed: Sep. 25, 1992

[51] Int. Cl.⁵ ............................................. A61B 17/00
[52] U.S. Cl. .................................. 128/837; 128/887; 606/119
[58] Field of Search ............... 604/902, 281, 34, 256, 604/269, 329–331, 355; 128/761–764, 769, 830–841, 883, 884, 887; 606/119–126

[56] References Cited

U.S. PATENT DOCUMENTS

| | | | |
|---|---|---|---|
| 2,440,521 | 4/1948 | Opperman, Sr. et al. | |
| 2,540,325 | 2/1951 | DeBray et al. | |
| 2,764,975 | 10/1956 | Greenberg | 604/174 |
| 2,836,177 | 5/1958 | Sells | 128/841 |
| 3,312,215 | 4/1967 | Silber | 128/841 |
| 4,198,981 | 4/1980 | Sinnreich . | |
| 4,381,771 | 5/1983 | Gabbay . | |
| 4,430,076 | 2/1984 | Harris | 606/119 |
| 5,082,005 | 1/1992 | Kaldany . | |
| 5,104,389 | 4/1992 | Deem et al. | 604/264 |
| 5,167,644 | 12/1992 | Fischell et al. | 604/264 |

FOREIGN PATENT DOCUMENTS 1035273 7/1966 United Kingdom ............... 604/282

Primary Examiner—Stephen C. Pellegrino
Assistant Examiner—Glenn K. Dawson
Attorney, Agent, or Firm—Darby & Darby

[57] ABSTRACT

A surgical diaphragm for use in laparoscopic gynecological surgery is illustrated and described. Proximal and distal tubes extend from the diaphragm with the end of the proximal tube being accessible to the surgeon. The diaphragm functions to maintain the pneumoperitoneum during laparoscopic surgery when a colpotomy is required. The proximal tube may be sealed in such a way as to permit fluid egress and ingress to the surgical site through the colpotomy, and also to permit surgical tools to be inserted through the tubes.

2 Claims, 1 Drawing Sheet

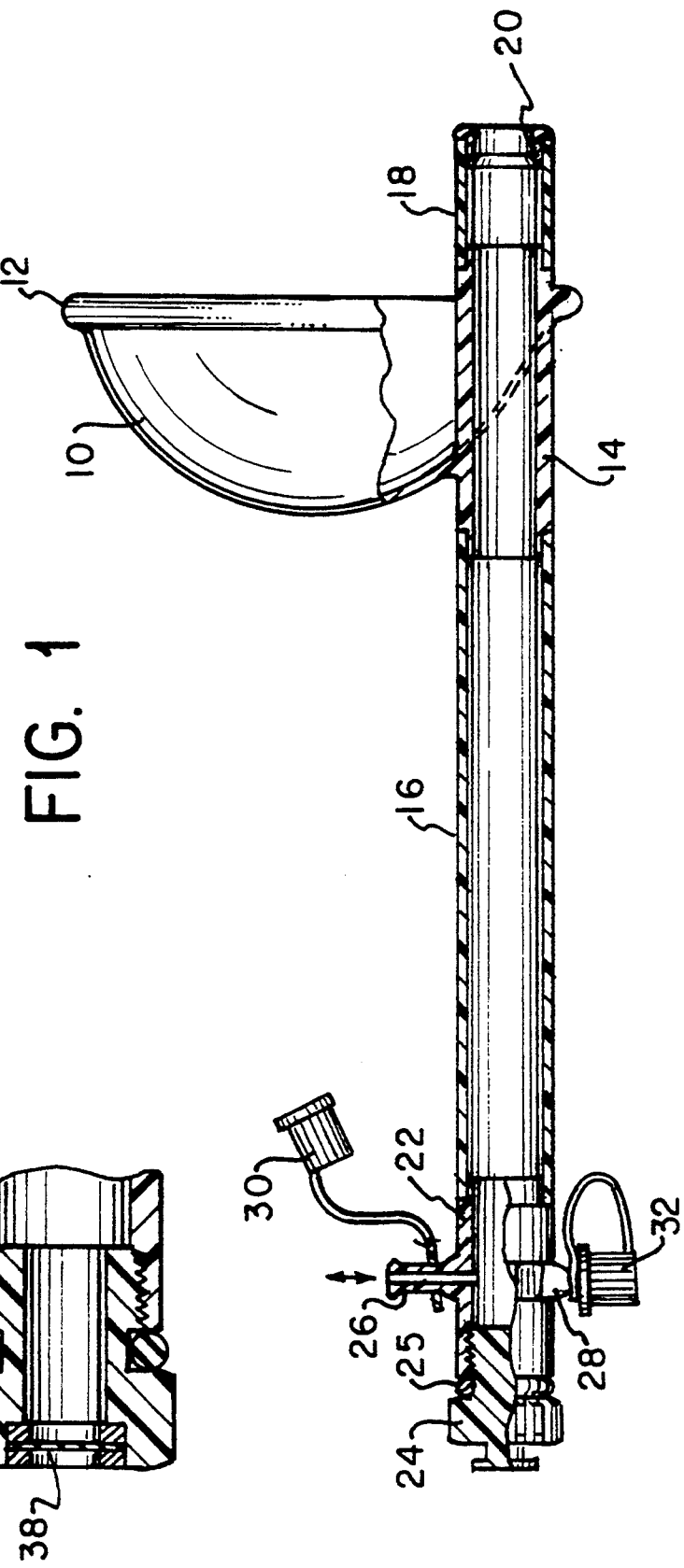

SURGICAL DIAPHRAGM FOR MAINTAINING THE PNEUMOPERITONEUM DURING A LAPAROSCOPIC PROCEDURE

This invention relates to a surgical diaphragm for use in laparoscopic gynecological operations.

Laparoscopic operations involve operations within the peritoneal cavity by means of instruments introduced into the cavity through tubular members or cannulas inserted through the abdominal wall. In such operations, a gas such as carbon dioxide is commonly pumped into the peritoneal cavity to create a space in which the surgeon can work. The presence of gas within the peritoneal cavity is known as the pneumoperitoneum.

In laparoscopy, several perforations are made in the patient's abdominal wall by means of trocars after which tubular members or cannulas are positioned in the openings formed by the trocars to permit the surgeon to view the operating site and to enable the surgery within the abdominal cavity. Laparoscopy provides advantages over conventional incision based surgery in that the perforations are less traumatic and result in faster recovery with concomitant benefits in terms of comfort and expense. Moreover, laparoscopic surgery is usually less time consuming and less expensive than incision based surgery.

Laparoscopy is today commonly used for various gynecological operations which very often involve the removal of tissues such as fibroid tumors, ovaries, ovarian cysts, etc. In some cases, the tissue is too large to be removed through the tubular members which have been passed through the abdominal wall, and it is known today to make an incision known as a colpotomy in the back of the vagina to enable the removal of tissue which cannot conveniently be removed through the existing tubular members. The colpotomy, however, creates an opening through which the pneumoperitoneum can escape and the loss of the pneumoperitoneum can present problems for the surgeon in attempting to complete the operation and to remove the excised tissue.

Thus, the object of the invention is to provide a surgical device for use in laparoscopic gynecological surgical procedures wherein the pneumoperitoneum is maintained despite the presence of a colpotomy.

A further object of the invention is to provide a surgical device of the type described wherein surgical instruments can be inserted vaginally through the colpotomy while maintaining the pneumoperitoneum.

A still further object of the invention is to provide a surgical diaphragm for use in laparoscopic gynecological procedures of the type described wherein materials such as blood clots can be removed from the abdominal cavity and fluids such as irrigating fluids introduced into the abdominal cavity through the colpotomy without destroying the pneumoperitoneum.

SUMMARY OF THE INVENTION

Briefly, in accordance with the invention, a diaphragm essentially identical to a contraceptive diaphragm is provided. A tube extends through the diaphragm, with the distal end of the tube positioned in proximity to the colpotomy and the proximal end of the tube being sufficiently long so that it extends outside of the patient. The external end of the proximal tube portion is sealed so that the pneumoperitoneum cannot be lost through the colpotomy. Sealed luers may be provided at the external end of the proximal tube portion to permit drainage of fluids from, and introduction of fluids to, the surgical site. When tissue is to be removed, the diaphragm may function as a surgical bag for collecting the tissue for subsequent removal through the vagina.

IN THE DRAWINGS

FIG. 1 is a side plan view partially in section of a preferred embodiment of a surgical diaphragm in accordance with the invention; and FIG. 2 is a side sectional view of a sealing member for use with the invention.

DETAILED DESCRIPTION

In the preferred embodiment, the invention comprises a diaphragm 10 which is dome-shaped and includes an outer supporting ring 12. The construction of diaphragm 10 is essentially the same as that of a standard contraceptive diaphragm.

In accordance with the invention, a flexible tube passes through the diaphragm 10. Various different constructions may be provided to achieve this objective. In the preferred embodiment, the diaphragm includes an integrally formed circular bulkhead 14 which is molded with the diaphragm during manufacture.

An elongated proximal tube 16 is bonded to the bulkhead at its proximal side and a shorter distal tube 18 is connected to the distal side of the bulkhead. A ring 20 is connected to the distal end of the distal tube 18 to prevent the tube from collapsing during use.

An annular hub 22 is bonded to the proximal end of the tube 16. The proximal end of hub 22 is threaded to receive a sealing cap 24 which can be screwed into the hub to provide a fluid type seal with the assistance of an O-ring 25. Hub 22 includes upper and lower luer fittings 26 and 28 spaced 180° apart. The luers 26 and 28 can be sealed by caps 30 and 32, respectively, when not in use. As illustrated, the caps 30 and 32 are connected to the luers by means of straps (not numbered) to avoid misplacement. The cap 24 may be similarly connected to the hub 22 by a string (not shown) to prevent misplacement when it is removed. Typically, the lower luer 28 would be used for drainage and/or irrigation purposes. The upper luer 26 can be used to evacuate gas, such as smoke from a cauterizing procedure, or to introduce the gas used for insuflation.

The diaphragm shown in FIG. 1 should be made from conventional biologically inert plastic materials of the type commonly used to make medical devices of this type. Tubes 16 and 18 may have an interior diameter of 12 mm, the total length of the distal and proximal tubes and the bulkhead being 6.375 inches in the preferred embodiment. The bulkhead 14, ring 20 and hub 22 may be made of a relatively rigid form sustaining plastic material such as ABS, and the parts may be bonded together with a conventional adhesive such as Loctite 495. The size of the diaphragm will depend on the patient, and may range from 65 mm to 85 mm in diameter.

It is contemplated that conventional laparoscopic instruments may be introduced through the surgical diaphragm shown in FIG. 1 for various purposes such as aspiration, suturing or the like. For this purpose, the cap 24 may be removed and replaced by the valve 36 shown in FIG. 2. The valve 36 includes a seal 38 of the type commonly used in laparoscopic procedures to enable the introduction of surgical tools through the tubular members placed in the abdominal wall. By way of example, the valve construction of the tube may be used to introduce suturing devices through the tubes 16 and 18 to suture the colpotomy at the conclusion of the operation without causing a loss of the pneumoperitoneum.

In addition to maintaining the pneumoperitoneum, the invention also provides a useful way of collecting tissue which must be removed following an operation. In this respect, the tissue can be passed through the colpotomy and placed within the dome-like diaphragm 10 where the tissue can be stored until the surgeon is ready to remove it.

The invention may be used for many different types of operations. By way of example, in the case of a salpingooophorectomy (removal of the fallopian tubes and ovaries), after the appropriate tubular members have been placed in the abdomen, the abdomen is inflated and the ovaries cut away in accordance with conventional laparoscopic surgical procedures. After the colpotomy is performed, the surgical diaphragm, in accordance with the invention, is inserted and positioned in the same way as a contraceptive diaphragm. Diaphragm 10 is highly flexible and can be wrapped around the bulkhead 14 and proximal tube 16 in order to be inserted into the vagina. The ovaries are then forced through the colpotomy incision into the diaphragm 10 with the pneumoperitoneum maintained by virtue of the sealed tube 16. The colpotomy incision may then be sutured by means of conventional instruments inserted through the valve 36 and the tubes 16 and 18. At the completion of the operation, the diaphragm containing the tissue which has been excised and stored within the vagina is removed.

Because the invention provides a simple way to maintain the pneumoperitoneum when it is necessary to perform a colpotomy, it will tend to enhance the use of colpotomies as a surgical procedure. This is generally desirable in many types of laparoscopic gynecological procedures in which vaginal access to a surgical site may be beneficial. As one example, where extensive blood clotting is encountered, removal of the clots through a colpotomy may be simpler and less time consuming than attempting to remove the clots through laparoscopic tubular members. In such cases, of course, the colpotomy would be performed at an earlier stage of the operation.

I claim:

1. A method of maintaining the pneumoperitoneum after a colpotomy incision has been made in the course of laparoscopic gynecological surgery, comprising the step of inserting a diaphragm into the patient's cervix to prevent the escape of gas through the vagina, said diaphragm including a tubular member extending therethrough to enable the passage of fluids and other materials across a barrier provided by said diaphragm, said diaphgram including means enabling a surgeon to selectively seal the tubular member.

2. A method according to claim 1, further including the step of unsealing and opening said tubular member, and introducing surgical tools into the vagina through said tubular member.

* * * * *